United States Patent [19]
de Castiglione et al.

[11] Patent Number: 4,491,541
[45] Date of Patent: Jan. 1, 1985

[54] PEPTIDES

[75] Inventors: Roberto de Castiglione; Luigia Gozzini, both of Milan; Pier C. Montecucchi, Turin; Giuseppe Perseo, Desio, all of Italy

[73] Assignee: Farmitalia Carlo Erba, Milan

[21] Appl. No.: 542,974

[22] Filed: Oct. 18, 1983

[30] Foreign Application Priority Data

Nov. 10, 1982 [GB] United Kingdom ............... 8232080
Apr. 20, 1983 [GB] United Kingdom ............... 8310719

[51] Int. Cl.³ ........................................... C07C 103/52
[52] U.S. Cl. ............................................. 260/112.5 R
[58] Field of Search ................................ 260/112.5 R

[56] References Cited

U.S. PATENT DOCUMENTS 3,247,179 4/1966 Schwyzer et al. ............ 260/112.5 R
4,043,993 8/1977 Tinney et al. ................. 260/112.5 R

*Primary Examiner*—Delbert R. Phillips
*Attorney, Agent, or Firm*—Oblon, Fisher, Spivak, McClelland & Maier

[57] ABSTRACT

A peptide of formula (I):

X-A-B-C-Trp-D-Y wherein
  X represents hydrogen, or a terminal nitrogn protecting group selecting from the group consisting of the acyl, aromatic oxycarbonyl, alkyl, aralkyl and aliphatic oxycarbonyl;
  A represent a valence bond or a L-α-amino acid residue;
  B represent a L-α-imino acid residue or a L-α-amino acid;
  C represent a L-α-imino acid residue or a neutral L-α-amino acid residue;
  D represents a valence bond or a L-α-amino acid residue; and
  Y represents hydroxy, an amino group or a group of the formula OR, NHR, NR$_2$ or NH—NH—R′, wherein R represents a straight chain, branched chain or cyclic (including fused or bridged ring) alkyl group having up to 11 carbon atoms, optionally being substituted; a phenyl group or an aralkyl group having from 7 to 9 carbon atoms; and R′ represents hydrogen, any of the groups which R may represent; a straight chain, branched chain or cyclic aliphatic acyl group having from 1 to 11 carbon atoms, optionally substituted by hydroxy, an amino group or a halogen atom; an aromatic acyl group, optionally substituted by hydroxy, amino, or a halogen atom; a straight chain, branched chain or cyclic aliphatic oxycarbonyl group having from 3 to 11 carbon atoms, or an aromatic oxycarbonyl group.

3 Claims, No Drawings

PEPTIDES

The present invention relates to biologically active peptides, their pharmaceutically acceptable salts, processes for their preparation and application as therapeutic agents.

(In this specification the symbols and abbreviations employed are those which are commonly used in peptide chemistry (see J. Biol. Chem. 1972, 247, 977–983). Boc, t-butyloxycarbonyl; Bzl, benzyl; c, concentration; d, decomposition; HOTcp, trichlorophenol; MeOH, methanol, Met(O), methionine sulfoxide; (4-Cl)Phe, 4-chloro-L-phenylalanine; (4-NH$_2$)Phe, 4-amino-L-phenylalanine; (4-NO$_2$)Phe, 4-nitro-L-phenylalanine; Pip, L-pipecolic acid; Thz, 4-L-thiazolidine carboxylic acid; TLC, thin layer chromatography.)

An object of the present invention is to provide a peptide which exhibits growth promoting activity.

Another object of the present invention is to provide a peptide which exhibits endocrinological activity.

The present invention provides peptides of the formula:

X-A-B-C-Trp-D-Y wherein

X represents hydrogen, a terminal nitrogn protecting group which is acyl, aromatic oxycarbonyl, alkyl, aralkyl or aliphatic oxycarbonyl;

A represents a valence bond or an L-α-amino acid residue;

B represents an L-α-imino acid residue or an L-α-amino acid residue;

C represents an L-α-imino acid residue or a neutral L-α-amino acid residue;

D represents a valence bond or an L-α-amino acid residue;

Y represents hydroxy, an amino group or a group of the formula OR, NHR, NR$_2$ or NH—NH—R′, wherein R represents a straight chain, branched chain or cyclic (including fused or bridged ring) alkyl group having up to 11 carbon atoms, optionally being substituted, a phenyl group or an aralkyl group having from 7 to 9 carbon atoms; and R′ represents hydrogen, any of the groups which R may represent; a straight chain, branched chain or cyclic aliphatic acyl group having from 1 to 11 carbon atoms, optionally substituted by hydroxy, an amino group or a halogen atom; an aromatic acyl group, optionally substituted by hydroxy, amino, or a halogen atom; a straight chain, branched chain or cyclic aliphatic oxycarbonyl group having from 3 to 11 carbon atoms, or an aromatic oxycarbonyl group.

In the above compound the preferred terminal nitrogen atom protecting groups which X may represent include, as acyl groups, formyl, acetyl, trifluoroacetyl, propionyl and benzoyl; as aromatic oxycarbonyl groups, which form a urethane group with the nitrogen atom, benzyloxycarbonyl, 4-nitrobenzyloxycarbonyl, 4-methoxybenzyloxycarbonyl, 2,4-dichlorobenzyloxycarbonyl, 2-bromobenzyloxycarbonyl, 9-fluorenylmethoxycarbonyl (Fmoc) and 3,5-dimethoxy-α,α-dimethylbenzyloxycarbonyl (Ddz) groups; as aliphatic oxycarbonyl groups, which form a urethane group with the nitrogen atom, t-butoxycarbonyl, 1-methylcyclobutoxycarbonyl, adamtanyloxycarbonyl and isobornyloxycarbonyl groups; and, as alkyl and aralkyl groups, trityl, benzyl, methyl and isopropyl groups.

Preferred L-α-amino acid residues which A may represent include Phe, (4-NO$_2$)Phe, (4-NH$_2$)Phe, (4-Cl)Phe, and Tyr. Preferred L-α-imino acid residues which B may represent include Pro, Thz and Pip. When A is absent from the molecule, preferred L-α-amino acid residues which B may represent include Pyr, Phe and Tyr. Preferred L-α-imino acid residues which C may represent include Pro, Thz and Pip. Preferred neutral L-α-amino acid residues which C may represent include Ala, Val and Leu. Preferred L-α-amino acid residues which D may represent include Val, Leu, Met, Met(O), Ile and Phe. Preferred groups which R may represent include methyl, ethyl, n-propyl, isopropyl, n-butyl, s-butyl, isobutyl, t-butyl, 2,2,2-trifluoroethyl, cyclohexyl, adamantyl, phenyl, benzyl and phenethyl groups.

Examples of acyl groups which R′ may represent are formyl, acetyl, trifluoroacetyl, propionyl, butyryl, adamantylcarbonyl, benzoyl, phenylacetyl and cinnamoyl. The aliphatic and aromatic oxycarbonyl groups which R′ may represent are preferably those groups mentioned as preferred terminal nitrogen protecting groups of substituent X which are aliphatic and aromatic oxycarbonyl groups.

Salts of the peptides of the present invention with pharmaceutically acceptable acids or bases are also within the scope of the invention. Suitable pharmaceutically acceptable acids include a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicylic, gluconic, ascorbic and related acids. Suitable pharmaceutically acceptable bases include a variety of inorganic and organic bases such as sodium hydroxide, potassium hydroxide, diethylamine, triethylamine and dicyclohexylamine.

The synthesis of the peptides of the present invention is accomplished by classical solution methods. The synthesis consists essentially in appropriate successive condensations of protected amino acids or peptides. The condensation is conducted so that the resulting peptides have the desired sequence of 4 or 5 amino acid residues. The amino acids and peptides, which are condensed according to known methods in polypeptide chemistry, have such of their amino and carboxyl groups that are not involved in the formation of peptide linkage, blocked by suitable protecting groups. The protecting groups are capable of being removed by known acidolysis, saponification or hydrogenolysis techniques.

For the protection of amino groups the following are examples of protective groups which may be employed: benzyloxycarbonyl, t-butoxycarbonyl, trityl, formyl, trifluoroacetyl, o-nitrophenylsulfenyl, 4-methoxybenzyloxycarbonyl 9-fluorenylmethoxycarbonyl and 3,5-dimethoxy-α,α-dimethylbenzyloxycarbonyl. For the protection of carboxy groups the following are examples of protective groups which may be employed: methyl, ethyl, t-butyl, benzyl and p-nitrobenzyl.

The condensation between an amino group of one molecule and the carboxyl group of another molecule to form a peptide linkage may be conducted through an activated acyl-derivative such as a mixed anhydride, an azide or an activated ester, or by direct condensation between a free amino group and a free carboxyl group, in the presence of a condensing agent such as dicyclohexylcarbodiimide, alone or together with a racemization preventing agent, such as N-hydroxysuccinimide or 1-hydroxybenzotriazole.

Hydrazido or substituted hydrazido derivatives of the present invention are prepared by the condensation of the N-protected peptide or amino acid with a suitably substituted hydrazine, such as benzylcarbazate, t-butylcarbazate, adamantylcarbazate, phenylhydrazine or adamantylhydrazine, or by reacting the N-protected peptide or amino acid hydrazide with a suitable alkylating agent such as an alkyl chloride, or with a suitable acylating agent such as benzylchloroformate, t-butylfluoroformate, di-t-butyldicarbonate or adamantylfluoroformate. The condensation may be carried out in a solvent such as dimethylformamide, pyridine, acetonitrile, tetrahydrofuran or N-methyl-2-pyrrolidone, and the reaction temperature may range from $-30°$ C. to ambient temperature. The reaction time is generally from 1 to 120 hours. The scheme of synthesis, the protecting groups and the condensation agents are selected so as to avoid the risk of racemization.

De-protecting reactions are carried out according to methods known per se in polypeptide chemistry. Peptides wherein Y represents OR are prepared, for example, starting from the C-terminal amino acid esterified by the appropriate alcohol. Peptides wherein Y represents OH can be prepared, for example, by hydrolysis of peptides wherein Y represents OR. Peptides wherein Y represents $NH_2$, NHR or $NR_2$ can be prepared by ammonolysis of the corresponding esters or by starting from a C-terminal amino acid amidated by an appropriate amine.

Biological Activity

The compounds described in the present invention possess interesting growth promoting activity in animals as indicated by the in vivo-in vitro test system on the protein synthesis of liver tissue as described by K. Kämmerer and A. Dey-Hazra in Veterinär-Medizinische Nachrichten, 99–112 (1980). They also show interesting endocrinological activity such as prolactin and luteinizing hormone release.

Evaluation of Growth Promoting Activity

The peptides of the present invention, for example H-Phe-Pro-Pro-Trp-Met-$NH_2$, were tested in rats in daily doses ranging from 1 to 100 ng/Kg administered subcutaneously for a period of one to four weeks. They showed an increase of liver protein synthesis as determined by the method of Kämmerer and Dey-Hazra and an increase of body weight at the end of the four weeks' experiments. In addition the feed conversion ratio was improved. For veterinary use, the administration of the compounds of this invention to food producing animals can be effected in a dose range from 1 to 100 ng/kg according to the usual veterinary techniques for treatment with anabolic or growth promoting agents, namely by subcutaneous implant or in a suitable stabilized form mixed through the feed. Accordingly, the invention further provides a pharmaceutical or veterinary composition comprising a compound of the invention or a pharmaceutically or veterinarily acceptable salt thereof in admixture with a pharmaceutically or veterinarily acceptable diluent or carrier. In addition, these preparations can have directed or delayed liberation of the active ingredient.

The preferred peptides according to the invention are:

Pyr-Pro-Trp-Met-OH
Pyr-Pro-Trp-Met-OMe
Pyr-Pro-Trp-Met-$NH_2$
Pyr-Pro-Trp-Met(O)-OH
Pyr-Pro-Trp-Met(O)-OMe
Pyr-Pro-Trp-Met(O)-$NH_2$
Pyr-Ala-Trp-Met-OH
Pyr-Ala-Trp-Met-OMe
Pyr-Ala-Trp-Met-$NH_2$
Pyr-Ala-Trp-Leu-OH
Pyr-Ala-Trp-Leu-OMe
Pyr-Ala-Trp-Leu-$NH_2$
Pyr-Pro-Trp-Val-OH
Pyr-Pro-Trp-Val-OMe
Pyr-Pro-Trp-Val-$NH_2$
H-Phe-Pro-Pro-Trp-OH
H-Phe-Pro-Pro-Trp-OMe
H-Phe-Pro-Pro-Trp-$NH_2$
H-Phe-Pro-Trp-Met-OMe
H-Phe-Pro-Trp-Met-$NH_2$
H-Tyr-Pro-Trp-Met-OH
H-Tyr-Pro-Trp-Met-OMe
H-Tyr-Pro-Trp-Met-$NH_2$
H-Tyr-Pro-Trp-Leu-OH
H-Tyr-Pro-Trp-Leu-OMe
H-Tyr-Pro-Trp-Leu-$NH_2$
H-Phe-Pro-Pro-Trp-Leu-OH
H-Phe-Pro-Pro-Trp-Leu-OMe
H-Phe-Pro-Pro-Trp-Leu-$NH_2$
H-Phe-Pro-Pro-Trp-Met-OH
H-Phe-Pro-Pro-Trp-Met-OMe
H-Phe-Pro-Pro-Trp-Met-$NH_2$
H-Phe-Pro-Pro-Trp-Val-OH
H-Phe-Pro-Pro-Trp-Val-OMe
H-Phe-Pro-Pro-Trp-Val-$NH_2$
H-Tyr-Pro-Pro-Trp-Met-OH
H-Tyr-Pro-Pro-Trp-Met-OMe
H-Tyr-Pro-Pro-Trp-Met-$NH_2$
H-(4-Cl)Phe-Pro-Pro-Trp-Met-OH
H-(4-Cl)Phe-Pro-Pro-Trp-Met-OMe
H-(4-Cl)Phe-Pro-Pro-Trp-Met-$NH_2$
H-(4-$NH_2$)Phe-Pro-Pro-Trp-Met-OH
H-(4-$NH_2$)Phe-Pro-Pro-Trp-Met-OMe
H-(4-$NH_2$)Phe-Pro-Pro-Trp-Met-$NH_2$

Having generally described this invention, a further understanding can be obtained by reference to certain specific examples which are provided herein for purposes of illustration only and are not intended to be limiting unless other specified.

The Rf values determined in the following examples were determined on pre-coated plates of silica gel 60 $F_{254}$ (Merck) having a layer thickness 0.25 mm, and a length of 20 cm using the following development systems:

System A: benzene/ethyl acetate/acetic acid/water = 100/100/20/10 by volume (upper phase).
System B: benzene/ethyl acetate/acetic acid/water = 100/100/40/15 by volume (upper phase).
System C: n-butanol/acetic acid/water = 4/1/1 by volume.
System D: chloroform/methanol/32% ammonium hydroxide = 55/45/20 by volume.

"E. Merck" is a trademark.

TLC analyses were not carried out under standard conditions. The Rf values can therefore change, particularly at different temperatures. Melting points were determined in open capillaries with a Tottoli apparatus and are uncorrected.

Most of the derivatives soften and decompose before melting. Solvents for crystallization, precipitation or grinding are reported in brackets. High voltage paper electrophoresis was carried out with a Pherograph-Original-Frankfurt Type 64 apparatus on Schleicher and Schüll Paper No. 2317 at pH 1.2 (formic acid:acetic acid:water=123:100:777) at 1600 V (40 V/cm), and at pH 5.8 (pyridine:acetic acid:water=450:50:4500) at 1400 V (32.5 V/cm). The products were characterized by their mobilities at pH 1.2 relative to Glu ($E_{1.2}$), and at pH 5.8 relative to His ($E_{5.8}$) or Glu, according to the migration direction.

EXAMPLE 1

Preparation of Pyr-Pro-Trp-Met-NH$_2$ (IV)

Step 1. Boc-Trp-Met-NH$_2$ (I)

To a solution of 3.043 g (10 mmol) of Boc-Trp-OH in 30 ml of anhydrous tetrahydrofuran, 1.12 ml (10 mmol) of N-methylmorpholine and 0.99 ml (10 mmol) of ethylchloroformate were successively added at a temperature of −12° C. After stirring for 2 minutes, a cold solution of 1.482 g (10 mmol) of H-Met-NH$_2$ (F. Chillemi, Gazz. Chim. Ital., 1963, 93, 1079) in 30 ml of dimethylformamide was added. The reaction mixture was stirred for 1 h at −12° C., and for 2 h at 0°-15° C., filtered to remove salts and evaporated in vacuo. The residue was dissolved in ethyl acetate and washed several times successively with sodium chloride saturated solutions of 1M citric acid, 1M sodium bicarbonate and water. The organic layer was dried over anhydrous sodium sulfate, and the solvent removed in vacuo.

A 4.041 g (93% yield) amount of compound I was obtained from ethyl acetate: m.p. 143° C., $[\alpha]_D^{20} = -12.3°$ (c=1 MeOH); Rf$_A$ 0.61; Rf$_B$ 0.84.

Step 2. HCl.H-Trp-Met-NH$_2$ (II)

A 3.911 g (9 mmol) amount of Boc-Trp-Met-NH$_2$ (I) was dissolved in 40 ml of formic acid at room temperature. After complete Boc-removal (TLC monitoring) the solvent was evaporated in vacuo at 30° C. The residue was dissolved in methanol cooled to 0° C., and 3.6 ml (10.8 mmol) of a 3M solution of hydrogen chloride in anhydrous tetrahydrofuran were added. Solvents were removed in vacuo, and 3 g (90% yield) of compound II were obtained from MeOH/AcOEt: m.p. 114° C. (D); $[\alpha]_D^{20} = +20.4°$ (c=1 MeOH): Rf$_C$ 0.62; $E_{1.2}$ 0.82.

Step 3. Pyr-Pro-OH (III)

A 3.604 g (10 mmol) amount of Z-Pyr-Pro-OH (R. de Castiglione et al, Gazz. Chim. Ital. 1964, 94, 875) dissolved in 30 ml of a mixture of methanol:dimethylformamide in a ratio of 1:1 were hydrogenated at room temperature and atmospheric pressure in the presence of 1.2 g of 10% by weight palladium on charcoal. The catalyst was removed by filtration and the solution concentrated in vacuo. A 2.149 g (95% yield) amount of compound III was obtained from diethyl ether: m.p. 168° C.; $[\alpha]_D^{20} = -105.1°$ (c=1 MeOH); Rf$_C$ 0.21; Rf$_D$ 0.652; $E_{5.8}$ 0.98, Glu.

Step 4. Pyr-Pro-Trp-Met-NH$_2$ (IV)

To a solution of 1.584 g (7 mmol) of Pry-Pro-OH (III) dissolved in 20 ml of anhydrous tetrahydrofuran, 0.79 ml (7 mmol) of N-methylmorpholine and 0.69 ml (7 mmol) of ethylchloroformate were successively added at −12° C. After stirring for 2 minutes, a cold solution of 2.596 g (7 mmol) of HCl.H-Trp-Met-NH$_2$ (II) and 0.79 ml (7 mmol) of N-methylmorpholine in 20 ml of dimethylformamide was added. The reaction mixture was stirred for 1 h at −12° C. and for 2 h at 0°-15° C., then filtered to remove salts and evaporated in vacuo. The crude product was purified by column chromatography on silica gel (Merck) 0.040-0.063 mm with an eluent of chloroform:methanol:water of 87:13:1 by volume. A 2.545 g (67% yield) amount of IV was obtained from diisopropyl ether: m.p. 207°-209° C., $[\alpha]_D^{23} = -95.3°$ (c=1 MeOH); Rf$_C$ 0.43. Amino acid ratio: Glu 1.00; Pro 0.98; Met 1.00.

EXAMPLE 2

Preparation of HCl.H-Phe-Pro-Pro-Trp-Met-NH$_2$ (IX)

Step 1. Boc-Phe-Pro-OH (V)

A 1.151 g (10 mmol) amount of proline was suspended in 10 ml of water and 10 ml 1N NaOH were added. The obtained solution was diluted with dimethylformamide, and the solvents were evaporated in vacuo. Dimethylformamide was added and again the solvent was evaporated in vacuo. A solution of Boc-Phe-OTcp (4.447 g, 10 mmol) (E. Sandrin and R. A. Boissonnas, Helv. Chim. Acta, 1963, 46, 1637) in 50 ml of dimethylformamide was added and the reaction mixture stirred at room temperature overnight. After solvent removal by evaporation in vacuo, the crude product was transformed into the corresponding free acid in the usual way and purified by column chromatography on silica gel (Merck) 0.040-0.063 mm with an eluent of chloroform:methanol in a ratio of 9:1 by volume. A 3.252 g amount of compound V (90% yield) was obtained as a foam by evaporation from petroleum ether: Rf$_A$ 0.67.

Step 2. Boc-Pro-Trp-Met-NH$_2$ (VI)

Starting from 1.722 g (8 mmol) of Boc-Pro-OH and 2.967 g (8 mmol) of HCl.H-Trp-Met-NH$_2$ (II) and operating as in Step 1 of Example 1, 3.828 g (90% yield) of VI were obtained from isopropyl alcohol: $[\alpha]_D^{20} = -70.2°$ (c=1 MeOH); Rf$_A$ 0.38; Rf$_B$ 0.73.

Step 3. HCl.H-Pro-Trp-Met-NH$_2$ (VII)

Starting from 3.722 g (7 mmol) of Boc-Pro-Trp-Met-NH$_2$ (VI) and operating as in Step 2 of Example 1, 2.621 g (80% yield) of VII were obtained from absolute ethyl alcohol; $[\alpha]_D^{20} = -23.0°$ (c=1 MeOH); Rf$_C$ 0.41; $E_{1.2}$ 0.76.

Step 4. Boc-Phe-Pro-Pro-Trp-Met-NH$_2$ (VIII)

A solution of 2.340 g (5 mmol) of HCl.H-Pro-Trp-Met-NH$_2$ (VII) in 20 ml of dimethylformamide was cooled to 0° C. and 0.56 ml of N-methylmorpholine were added, followed by 1.812 g of Boc-Phe-Pro-OH (V) of 0.676 g (5 mmol) of 1-hydroxy-benzotriazole and 1.135 g (5.5 mmol) of dicyclohexylcarbodiimide. The reaction mixture was stirred at room temperature for 3 hours then filtered and evaporated in vacuo. The crude product was purified by column chromatography on silica gel (Merck) 0.040-0.063 mm with an eluent of ethyl acetate:methanol:water in a ratio of 70:30:2 by volume. A 1.940 g (50% yield) amount of compound (VIII) was obtained from ethyl acetate/diethyl ether: Rf$_A$ 0.15; Rf$_B$ 0.60.

Step 5. HCl.H-Phe-Pro-Pro-Trp-Met-NH$_2$ (IX)

Starting from 1.552 g (2 mmol) of Boc-Phe-Pro-Trp-Met-NH$_2$ (VIII) and operating as in Step 2 of the Example 1, a 1.282 g amount of crude product was obtained. The crude product was purified by column chromatography on silica gel (Merck) 0.040-0.063 mm eluting with chloroform:methanol=82:18 by volume. A 0.705 g amount of compound IX (50% overall yield)

was obtained from methanol/diethyl ether: m.p. 205°–215° C. (d), $[\alpha]_D^{20} = -79.8°$ (c=1 MeOH); $Rf_C$ 0.39; $E_{1.2}$ 0.61. Amino acid ratio: Pro 1.99; Met 1.00; Phe 1.00.

EXAMPLE 3

Preparation of Pyr-Pro-Trp-Val-OMe (XII)

Step 1. Boc-Trp-Val-OMe (X)

To a solution of 12.17 g (40 mmol) of Boc-Trp-OH in 100 ml of anhydrous tetrahydrofuran, 4.5 ml (40 mmol) of N-methyl-morpholine and 3.96 ml (40 mmol) of ethylchloroformate were successively added at a temperature of −12° C. After stirring for 2 minutes, a cold solution of 6.70 g (40 mmol) of HCl.H-Val-OMe (E. L. Smith et al, J. Biol. Chem. 199, 801, 1952) and 4.5 ml of N-methylmorpholine (40 mmol) in 50 ml of dimethylformamide was added. The reaction mixture was stirred for 1 h at −12° C. and 2 h at 0°–15° C., filtered to remove salts and evaporated in vacuo. The residue was dissolved in ethyl acetate and washed several times successively with sodium chloride saturated solutions of 1M citric acid, 1M sodium bicarbonate and water. The organic layer was dried over anhydrous sodium sulfate and the solvent removed in vacuo.

A 14.1 g (84.4% yield) amount of compound (X) was obtained from isopropyl alcohol/diisopropyl ether. $Rf_A$ 0.81; $Rf_b$ 0.87.

Step 2. HCl.H-Trp-Val-OMe (XI)

A 12.52 g (30 mmol) amount of Boc-Trp-Val-OMe (X) was dissolved in 15 ml of formic acid at room temperature. After complete Boc-removal (TLC monitoring) the solvent was evaporated in vacuo at 30° C. The residue was dissolved in methanol cooled to 0° C., and 11 ml (33 mmol) of a 3M solution of hydrogen chloride in anhydrous tetrahydrofuran were added. Solvents were removed in vacuo and 9.55 g (90% yield) of compound II were obtained from isopropyl alcohol/diisopropyl ether. $Rf_C$ 0.69, $E_{1.2}$ 0.89 Glu.

Step 3. Pyr-Pro-Trp-Val-OMe (XII)

To a solution of 5.66 g (25 mmol) of Pyr-Pro-OH (III) in 60 ml of anhydrous tetrahydrofuran, 2.81 ml (25 mmol) N-methyl-morpholine and 2.48 ml (25 mmol) of ethylchloroformate were successively added at −12° C. After stirring for 2 minutes, a cold solution of 8.85 g (25 mmol) of HCl.H-Trp-Val-OMe (XI) and 2.81 ml (25 mmol) of N-methylmorpholine in 60 ml of dimethylformamide was added. The reaction mixture was stirred for 1 h at −12° C. and for 2 h at 0°–15° C., then filtered to remove salts and evaporated in vacuo. The crude product was purified by column chromatography on silica gel (Merck) 0.040–0.063 mm with an eluent of methylene dichloride:methanol:water in a ratio of 92:8:1 by volume. A 8.37 g (63.7% yield) amount of XII was obtained from isopropyl alcohol/diisopropyl ether. m.p. 120° C. $[\alpha]_D^{24} = -76.3°$ (c=1 MeOH); $Rf_B$ 0.21; $Rf_C$ 0.56; Amino acid ratio:Glu 1.00; Pro 0.98; Val 1.00.

EXAMPLE 4

Preparation of Pyr-Pro-Trp-Val-OH (XIII)

A 2.63 g (5 mmol) amount of Pyr-Pro-Trp-Val-OMe (XII), prepared in Example 3, Step 3, were dissolved in 15 ml of methanol and saponified with 7.5 ml 1N sodium hydroxide at room temperature. The reaction was completed within 4 hrs. The solution was diluted with 40 ml of water and concentrated in vacuo to half the volume, diluted again with 40 ml of water, cooled to 0° C., acidified with a 5N hydrochloric acid to pH 2 and finally extracted with ethyl acetate. The organic layer was washed to neutrality with sodium chloride saturated solutions, dried over anhydrous sodium sulfate and the solvent removed in vacuo. A 2.1 g 82% yield) amount of compound (XIII) was obtained from isopropyl alcohol/diisopropyl ether. $[\alpha]_D^{25} = -47.6°$ (c=1 MeOH); $Rf_B$ 0.11; $Rf_C$ 0.48; $E_{5.8}$ 0.43 Glu. Amino acid ratio Glu 1.00; Pro 0.99; Val 1.00.

EXAMPLE 5

Preparation of Pyr-Pro-Trp-Val-NH₂ (XIV)

A 2.63 g (5 mmol) amount of Pyr-Pro-Trp-Val-OMe (XII) prepared in Example 3, Step 3, was dissolved in 20 ml of methanol and 0.4 ml (2% v/v) of ethylene glycol. The solution was saturated at 5° C. with gaseous ammonia and kept in the refrigerator until completion of the reaction (TLC monitoring). Excess ammonia was removed under vacuum and the solution concentrated in vacuo. After purification by column chromatography (silica gel 0.040–0.063 mm; eluent system $CH_2Cl_2$:MeOH=87.13), the desired compound XIV was obtained (1.99 g, 78% yield) from isopropyl alcohol/diisopropyl ether. m.p. 128° C.; $[\alpha]_D^{24} = -69.3°$ (c=1 MeOH); $Rf_B$ 0.10; $Rf_C$ 0.43. Amino acid ratio:Glu 0.99; Pro 0.97; Val 1.00.

Operating as in previous Examples, the following additional peptides have been synthesized:

(XV)H-Phe-Pro-Pro-Trp-Leu-NH₂.HCl $RF_C$ 0.43; $E_{1.2}$ 0.61.

(XVI)Pyr-Ala-Trp-Met-OH $Rf_C$ 0.57.

(XVII)Pyr-Pro-Trp-Met-OH $Rf_C$ 0.42.

(XVIII)H-Tyr-Pro-Trp-Leu-NH₂.HCl m.p. 160°–170° C. (d) (methanol/diethylether); $E_{1.2}$ 0.63.

(XIX)H-Phe-Pro-Trp-Ile-NH₂.HCl m.p. 125°–130° C. (d) (diethyl ether); $E_{1.2}$ 0.60.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A peptide of formula (I):

X-A-B-C-TRP-D-Y wherein

X represents hydrogen, or a terminal nitrogen protecting group selected from formyl, acetyl, trifluoroacetyl, proprionyl, benzoyl, benzyloxycarbonyl, 4-nitrobenzyloxy carbonyl, 4-methoxy-benzyloxycarbonyl, 2, 4, - dichlorobenzyloxy carbonyl, 2-bromobenzyloxycarbonyl, 9-fluorenylmethoxy carbonyl, 3,5-dimethoxy - α α 'dimethylbenzyloxycarbonyl, t-butoxycarbonyl, 1-methylcyclobutoxycarbonyl, adamantyloxy carbonyl, isobornyloxy-carbonyl, trityl, benzyl, methyl and isopropyl groups;

A represents a valence bond or an L-α-amino acid residue selected from Phe, Tyr, (4-Cl) Phe and (4-NH₂) Phe residues;

B represents an L-α-imino acid residue or an L-α-amino acid residue selected from Pro, Pyr, Phe and Tyr residues;

C represents an L-α-imino acid residue or a neutral L-α-amino acid residue selected from Pro and Ala residues;

D represents a valence bond or an L-α-amino acid residue selected from Leu, Val, Met, Met(O), Ile and Phe; and, Y represents hydroxy, an amino group or a group of the formula OR, NHR, $NR_2$ or NH—NH—R', wherein R represents a group selected from methyl, ethyl, n-propyl, isopropyl, n-butyl, s-butyl, isobutyl, t-butyl 2,2,2-trifluoroethyl, cyclohexyl, adamantyl, phenyl, benzyl and phenethyl group, R' represents a hydrogen atom, any of the groups specifically named in this claim for R, or a formyl, acetyl, trifluoroacetyl, propionyl, butyryl, adamantylcarbonyl, benzoyl, phenylacetyl, cinnamyl, benzyloxycarbonyl, 4-nitrobenzyloxycarbonyl, 4-methoxybenzyloxy-carbonyl, 2,4-dichlorobenzyloxycarbonyl, 2-bromobenzyloxycarbonyl, 9-fluorenylmethoxycarbonyl, 3,5-dimethoxy-α α'dimethylbenzyloxycarbonyl, t-butoxycarbonyl, 1-methyl-cyclobutoxycarbonyl, adamantyloxycarbonyl or isobornyloxycarbonyl group; and the pharmaceutically or veterinarily acceptable salt thereof.

2. The peptide H-Tyr-Pro-Trp-Met-$NH_2$ or H-Phe-Pro-Pro-Trp-Met-$NH_2$ or a pharmaceutically or veterinarily acceptable salt thereof.

3. The compound wherein the peptide chain is:
Pyr-Pro-Trp-Met-OH
Pyr-pro-Trp-Met-OMe
Pyr-Pro-Trp-Met-$NH_2$
Pyr-Pro-Trp-Met(O)-OH
Pyr-Pro-Trp-Met(O)-OMe
Pyr-Pro-Trp-Met(O)-$NH_2$
Pyr-Ala-Trp-Met-OH
Pyr-Ala-Trp-Met-OMe
Pyr-Ala-Trp-Met-$NH_2$
Pyr-Ala-Trp-Leu-OH
Pyr-Ala-Trp-Leu-OMe
Pyr-Ala-Trp-Leu-$NH_2$
Pyr-Pro-Trp-Val-OH
Pyr-Pro-Trp-Val-OMe
Pyr-Pro-Trp-Val-$NH_2$
H-Phe-Pro-Pro-Trp-OH
H-Phe-Pro-Pro-Trp-OMe
H-Phe-Pro-Pro-Trp-$NH_2$
H-Phe-Pro-Trp-Met-OMe
H-Phe-Pro-Trp-Met-$NH_2$
H-Tyr-Pro-Trp-Met-OH
H-Tyr-Pro-Trp-Met-OMe
H-Tyr-Pro-Trp-Leu-OH
H-Tyr-Pro-Trp-Leu-OMe
H-Tyr-Pro-Trp-Leu-$NH_2$
H-Phe-Pro-Pro-Trp-Leu-OH
H-Phe-Pro-Pro-Trp-Leu-OMe
H-Phe-Pro-Pro-Trp-Leu-$NH_2$
H-Phe-Pro-Pro-Trp-Met-OH
H-Phe-Pro-Pro-Trp-Met-OMe
H-Phe-Pro-Pro-Trp-Met-$NH_2$
H-Phe-Pro-Pro-Trp-Val-OH
H-Phe-Pro-Pro-Trp-Val-OMe
H-Phe-Pro-Pro-Trp-Val-$NH_2$
H-Tyr-Pro-Pro-Trp-Met-OH
H-Tyr-Pro-Pro-Trp-Met-OMe
H-Tyr-Pro-Pro-Trp-Met-$NH_2$
H-(4-Cl)Phe-Pro-Pro-Trp-Met-OH
H-(4-Cl)Phe-Pro-Pro-Trp-Met-OMe
H-(4-Cl)Phe-Pro-Pro-Trp-Met-$NH_2$
H-(4-$NH_2$)Phe-Pro-Pro-Trp-Met-OH
H-(4-$NH_2$)Phe-Pro-Pro-Trp-Met-OMe or
H-(4-$NH_2$)Phe-Pro-Pro-Trp-Met-$NH_2$.

* * * * *